US010998095B2

(12) United States Patent
Vairavan et al.

(10) Patent No.: US 10,998,095 B2
(45) Date of Patent: May 4, 2021

(54) TOOL FOR RECOMMENDATION OF VENTILATION THERAPY GUIDED BY RISK SCORE FOR ACUTE RESPIRATOR DISTRESS SYNDROME (ARDS)

(71) Applicant: KONINKLIJKE PHILIPS N.V., Eindhoven (NL)

(72) Inventors: Srinivasan Vairavan, Ossining, NY (US); Nicolas Wadih Chbat, White Plains, NY (US); Caitlyn Marie Chiofolo, New Hyde Park, NY (US)

(73) Assignee: Koninklijke Philips N.V., Eindhoven (NL)

(*) Notice: Subject to any disclaimer, the term of this patent is extended or adjusted under 35 U.S.C. 154(b) by 384 days.

(21) Appl. No.: 15/564,464

(22) PCT Filed: Mar. 18, 2016

(86) PCT No.: PCT/IB2016/051525
§ 371 (c)(1),
(2) Date: Oct. 5, 2017

(87) PCT Pub. No.: WO2016/162769
PCT Pub. Date: Oct. 13, 2016

(65) Prior Publication Data
US 2018/0071470 A1 Mar. 15, 2018

Related U.S. Application Data

(60) Provisional application No. 62/144,559, filed on Apr. 8, 2015.

(51) Int. Cl.
*A61M 16/00* (2006.01)
*G16H 20/40* (2018.01)
(Continued)

(52) U.S. Cl.
CPC ........ *G16H 20/40* (2018.01); *A61M 16/0051* (2013.01); *A61M 16/0063* (2014.02);
(Continued)

(58) Field of Classification Search
CPC ................... A61B 5/08; A61B 5/4836; A61B 5/0803–097; A61M 16/026;
(Continued)

(56) References Cited

U.S. PATENT DOCUMENTS 8,638,200 B2  1/2014  Milne et al.
9,861,299 B1*  1/2018  Jones ............... A61B 5/7275
(Continued)

FOREIGN PATENT DOCUMENTS

WO  2009098627 A1  8/2009
WO  2013121374 A2  8/2013

OTHER PUBLICATIONS

Raghavendran et al; Ali and ARDS: Challenges and Advances; Crit Care Clin, Jul. 1, 2011; 27(3): 429-437. (Year: 2011).*
(Continued)

*Primary Examiner* — Devin B Henson
*Assistant Examiner* — H. Q. Nguyen
(74) *Attorney, Agent, or Firm* — Daniel H. Brean (57) ABSTRACT

Disclosed herein are approaches for monitoring a patient in real-time for ARDS development and providing a biomarker-driven ventilation therapy recommendation tool based on the correlation of various therapy patterns and an ARDS biomarker score. When the ARDS biomarker indicates that a patient has a high ARDS risk, the recommendation tool suggests possible therapy routes based on clinical practice. In response to a high score output by the ARDS detection model, the tool outputs a recommendation to initiate a lung protective ventilation strategy (Low Tidal Volume, high Positive End-Expiratory Pressure (PEEP)). A
(Continued)

high ARDS score is recognized to be predictive of the appropriateness of such therapy up to several hours before such intervention is typically initiated under current clinical practices.

15 Claims, 6 Drawing Sheets

(51) Int. Cl.
 *G16H 70/20* (2018.01)
 *A61M 16/10* (2006.01)
(52) U.S. Cl.
 CPC .......... *A61M 16/026* (2017.08); *A61M 16/10* (2013.01); *G16H 70/20* (2018.01)
(58) Field of Classification Search
 CPC .............. A61M 16/021; A61M 16/022; A61M 16/024; A61M 16/201–202; A61M 16/0096
 USPC ........................................ 128/204.18–204.24
 See application file for complete search history.

(56) References Cited

U.S. PATENT DOCUMENTS

| | | |
|---|---|---|
| 2011/0029248 A1 | 2/2011 | Saeed et al. |
| 2011/0224567 A1* | 9/2011 | Al-Ali ................. A61B 5/6833 600/529 |
| 2012/0145152 A1* | 6/2012 | Lain ........................ G06F 19/34 128/204.23 |
| 2012/0216809 A1 | 8/2012 | Milne et al. |
| 2014/0236035 A1 | 8/2014 | Milne et al. |
| 2015/0025405 A1* | 1/2015 | Vairavan ............. G06F 19/3418 600/529 |
| 2017/0232214 A1* | 8/2017 | Walsh ............... A61M 16/0051 128/202.22 |
| 2018/0071470 A1* | 3/2018 | Vairavan ............. G06F 19/3481 |

OTHER PUBLICATIONS

Trillo et al; Acute Lung Injury Prediction Score: Derivation and Validation in a Population Based Sample); Eur Respir J 2011; 37: 604-609. (Year: 2011).*

Rouby et al; Mechanical Ventilation in Patients with Acute Respiratory Distress Syndrome; Anesthesiology 2004; 101: 228-234. (Year: 2004).*

Pepe et al: "Early Prediction of the Adult Respiratory Distress Syndrome by a Simple Scoring Method"; Ann Emerg Med. Dec. 1983, vol. 12(12):749-55.

Neto et al: "Association Between Use of Lung-Protective Ventilation With Lower Tidal Volumes and Clinical Outcomes Among Patients Without Acute Respiratory Distress Syndrome: A Meta-Analysis"; JAMA 308.16 ( 2012): 1651-1659.

Amato et al: "Effect of a Protective-Ventilation Strategy on Mortality in the Acute Respiratory Distress Syndrome"; New England Journal of Medicine 338.6 (1998): 347-354.

* cited by examiner

TOOL FOR RECOMMENDATION OF VENTILATION THERAPY GUIDED BY RISK SCORE FOR ACUTE RESPIRATOR DISTRESS SYNDROME (ARDS)

CROSS-REFERENCE TO PRIOR APPLICATIONS

This application is the U.S. National Phase application under 35 U.S.C. § 371 of International Application No. PCT/I132016/051525, filed on Mar. 18, 2016, which claims the benefit of U.S. Provisional Patent Application No. 62/144,599, filed on Apr. 8, 2015. These applications are hereby incorporated by reference herein.

BACKGROUND

The following relates to the medical monitoring arts, clinical decision support system arts, intensive care monitoring and patient assessment arts, patient mechanical ventilation arts, and so forth.

Acute Respiratory Distress Syndrome (ARDS) is a devastating complication of acute illness and one of the leading causes of multiple organ failure and mortality in the intensive care unit (ICU). Acute Respiratory Distress Syndrome (ARDS) is estimated to be prevalent in 7-10% of all ICU patients, and exhibits a high mortality of greater than 40% after hospital discharge. However, less than one-third of ARDS patients are detected by ICU physicians. Various embodiments of ARDS detection are set forth in Vairavan et al., Int'l Appl. Pub. No. WO 2013/121374 A2 published Aug. 22, 2013 which is incorporated herein by reference in its entirety.

BRIEF SUMMARY

The following contemplates improved apparatuses and methods that overcome the aforementioned limitations and others.

According to one aspect, a therapy guidance tool for acute respiratory distress syndrome intensive care settings comprising one or more processors configured to use an ARDS score as a biomarker to recommend therapy.

According to another aspect, a method for guiding acute respiratory distress syndrome intensive care settings, comprising an ARDS score as a biomarker to recommend therapy.

According to another aspect, An apparatus for recommending ventilation strategy for a patient at risk for acute respiratory distress syndrome, comprising: a bedside monitor to monitor patient physiological variables; and one or more processors configured to: compute predictive inferences based on an ARDS score analyzed at a given time; continuously monitor a current ARDS score of a patient for the computed predictive inferences to determine a likely expected ARDS in the future; and generate an alert after determining a likely expected ARDS.

One advantage resides in real-time alerts of ARDS risk.

Another advantage resides in continuous monitoring of an ARDS biomarker.

Another advantage resides in suggesting ventilator settings for interventional therapy.

Numerous additional advantages and benefits will become apparent to those of ordinary skill in the art upon reading the following detailed description.

BRIEF DESCRIPTION OF THE DRAWINGS

The present application may take form in various components and arrangements of components, and in various process operations and arrangements of process operations. The drawings are only for the purpose of illustrating preferred embodiments and are not to be construed as limiting the present application.

DETAILED DESCRIPTION

Techniques disclosed herein use a continuous score of ARDS risk output by an ARDS detection model as a biomarker for ARDS development. The present application includes a biomarker-driven therapy recommendation tool based on the correlation of various therapy patterns and the biomarker itself (ARDS score). When the biomarker indicates that a patient has a high ARDS risk, the recommendation tool suggests possible therapy routes based on clinical practice. A high score in the ARDS detection model correlates well with the lung protective ventilation strategy (Low Tidal Volume, high Positive End-Expiratory Pressure (PEEP)), thus the tool indicates that lung protective therapy should be applied to the patient. A high ARDS score also has the capacity to predict the therapy several hours before the actual intervention. Such information, when computerized, into therapy recommendations enables continuous disease monitoring and improved adoption of best clinical practices, while supporting clinicians in planning prophylactic and interventional treatments.

Figure 1:
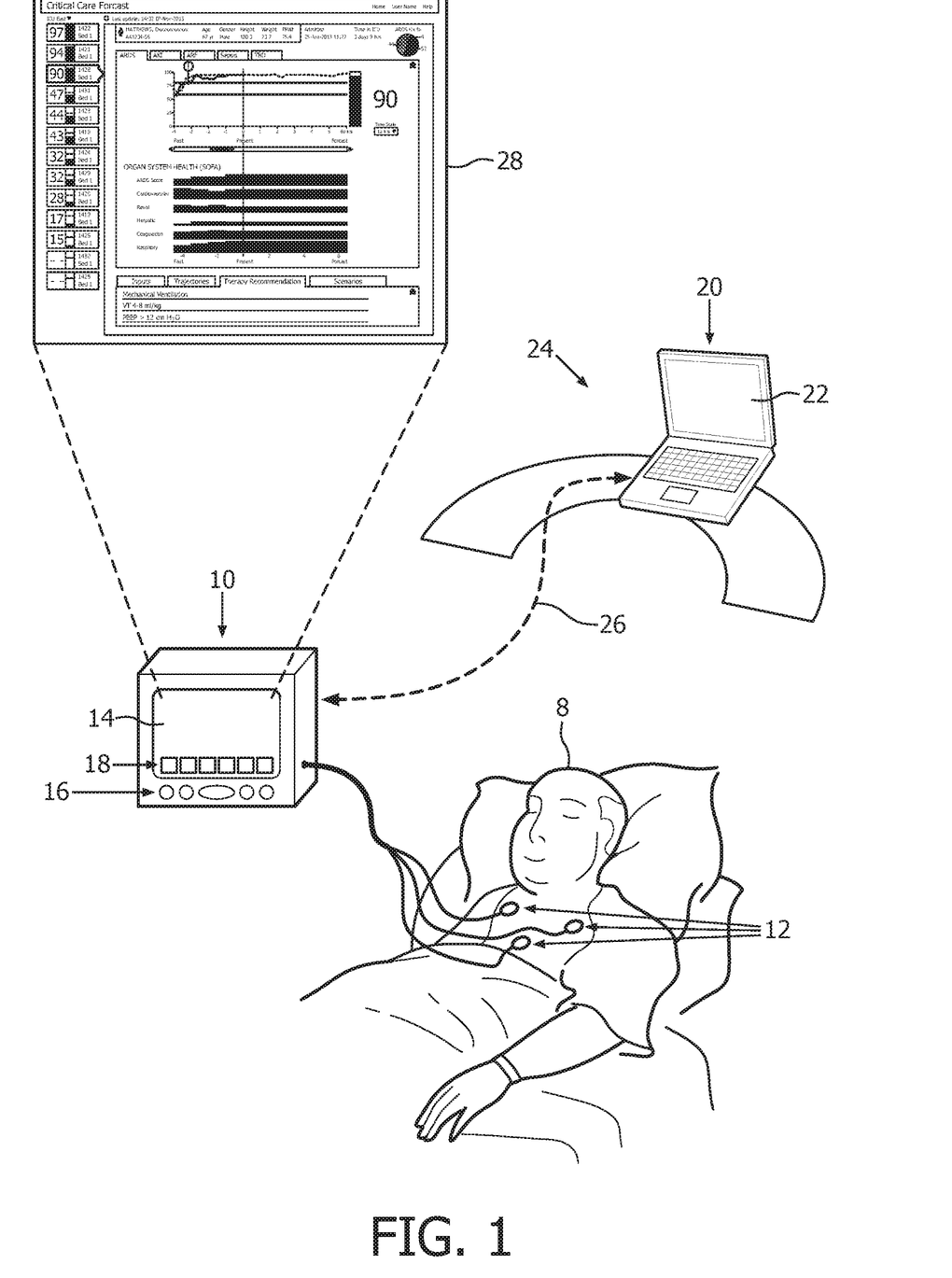
FIG. 1 diagrammatically shows a patient in an intensive care unit (ICU) being monitored for acute respiratory distress syndrome (ARDS) at a bedside monitor and at a nurses' station, the latter along with other patients in the ICU.

With reference to FIG. 1, a patient 8 is monitored by a bedside patient monitor 10, which displays trend data for various physiological variables of the patient 8. (Terms such as "physiological variables", "vital signs", or "vitals" are used interchangeably herein). For example, illustrative electrocardiograph (ECG) electrodes 12 suitably monitor heart rate and optionally full ECG traces as a function of time. Substantially any physiological variables of medical interest may be monitored, such as by way of illustrative example, one or more of the following: heart rate (HR); respiration rate (RR); systolic blood pressure (SBP); diastolic blood pressure (DBP); fraction of inspired oxygen ($FiO_2$); partial pressure of oxygen in arterial blood ($PaO_2$); positive end-expiratory pressure (PEEP); blood hemoglobin (Hgb); and so forth. Although not shown in FIG. 1, it is contemplated for the patient 8 to be on a mechanical ventilator.

The patient monitor 10 includes a display 14, which is preferably a graphical display, on which physiological variables and optionally other patient data are displayed using numeric representations, graphical representations, trend lines, or so forth. The patient monitor 10 further includes one or more user input devices, such as illustrative controls 16 mounted on the body of the monitor 10, a set of soft keys 18 shown on the display 14 (which is suitably a touch-sensitive display in such a configuration), a pull-out keyboard, various combinations thereof, or so forth. The user input device(s)

enable a nurse or other medical person to configure the monitor 10 (e.g. to select the physiological variables or other patient data to be monitored and/or displayed), to set alarm settings, or so forth. Although not explicitly shown, the patient monitor 10 may include other features such as a speaker for outputting an audio alarm if appropriate, one or more LEDs or lamps of other types to output visual alarms, and so forth.

The patient monitor 10 is an "intelligent" monitor in that it includes or is operatively connected with data processing capability provided by a microprocessor, microcontroller, or the like connected with suitable memory and other ancillary electronics (details not illustrated). In some embodiments the patient monitor 10 includes internal data processing capability in the form of a built-in computer, microprocessor, or so forth, such that the patient monitor can perform autonomous processing of monitored patient data. In other embodiments the patient monitor is a "dumb terminal" that is connected with a server or other computer or data processing device that performs the processing of patient data. It is also contemplated for a portion of the data processing capability to be distributed amongst intercommunicating body-worn sensors or devices mounted on the patient 8, e.g. in the form of a Medical Body Area Network (MBAN).

In illustrative examples, the patient 8 is disposed in a patient room of an intensive care unit (ICU), which may for example be a medical ICU (MICU), a surgical ICU (SICU), a cardiac care unit (CCU), a triage ICU (TRICU), or so forth. In such settings, the patient is typically monitored by the bedside patient monitor 10 located with the patient (e.g., in the patient's hospital room) and also by an electronic monitoring device 20 with suitable display 22 (e.g. a dedicated monitor device or a suitably configured computer) located at a nurses' station 24. Typically, the ICU has one or more such nurses' stations, with each nurses' station assigned to a specific set of patients (which may be as few as a single patient in extreme situations). A wired or wireless communication link (indicated diagrammatically by double-arrow-headed curved line 26) conveys patient data acquired by the bedside patient monitor 10 to the electronic monitoring device 20 at the nurses' station 24. The communication link 26 may, for example, comprise a wired or wireless Ethernet (dedicated or part of a hospital network), a Bluetooth connection, or so forth. It is contemplated for the communication link 26 to be a two-way link—i.e., data also may be transferrable from the nurses' station 24 to the bedside monitor 10.

The bedside patient monitor 10 is configured to detect and indicate Acute Respiratory Distress Syndrome (ARDS) by performing data processing as disclosed herein on information including at least one or more physiological variables monitored by the patient monitor 10. The display 14 of the bedside patient monitor 10 displays an ARDS ventilation tool 28 described in detail below. Additionally or alternatively, the electronic monitoring device 20 at the nurses' station 24 may be configured to detect and indicate ARDS by performing data processing as disclosed herein on information including at least one or more physiological variables monitored by the patient monitor 10 and display the ARDS ventilation tool 28. Note that the terms Acute Lung Injury (ALI) and Acute Respiratory Distress Syndrome (ARDS) are used interchangeably herein. Advantageously, the ARDS detection as disclosed herein is based on physiological variables such as heart rate (HR), respiratory rate (RR), systolic blood pressure (SBP), diastolic blood pressure (DBP), fraction of inspired oxygen ($FiO_2$), positive end-expiratory pressure (PEEP), or so forth, which are monitored by the patient monitor 10 and hence are available in real-time. Patient data with longer acquisition latency times, such as radiography reports and laboratory findings (e.g. $PaO_2$, Hgb, et cetera) are not utilized or are utilized as supplemental information for evaluating whether ARDS is indicated. In illustrative ARDS scoring examples presented herein, the data input to the ARDS model included vital signs, laboratory results and ventilator settings.

Figure 2:
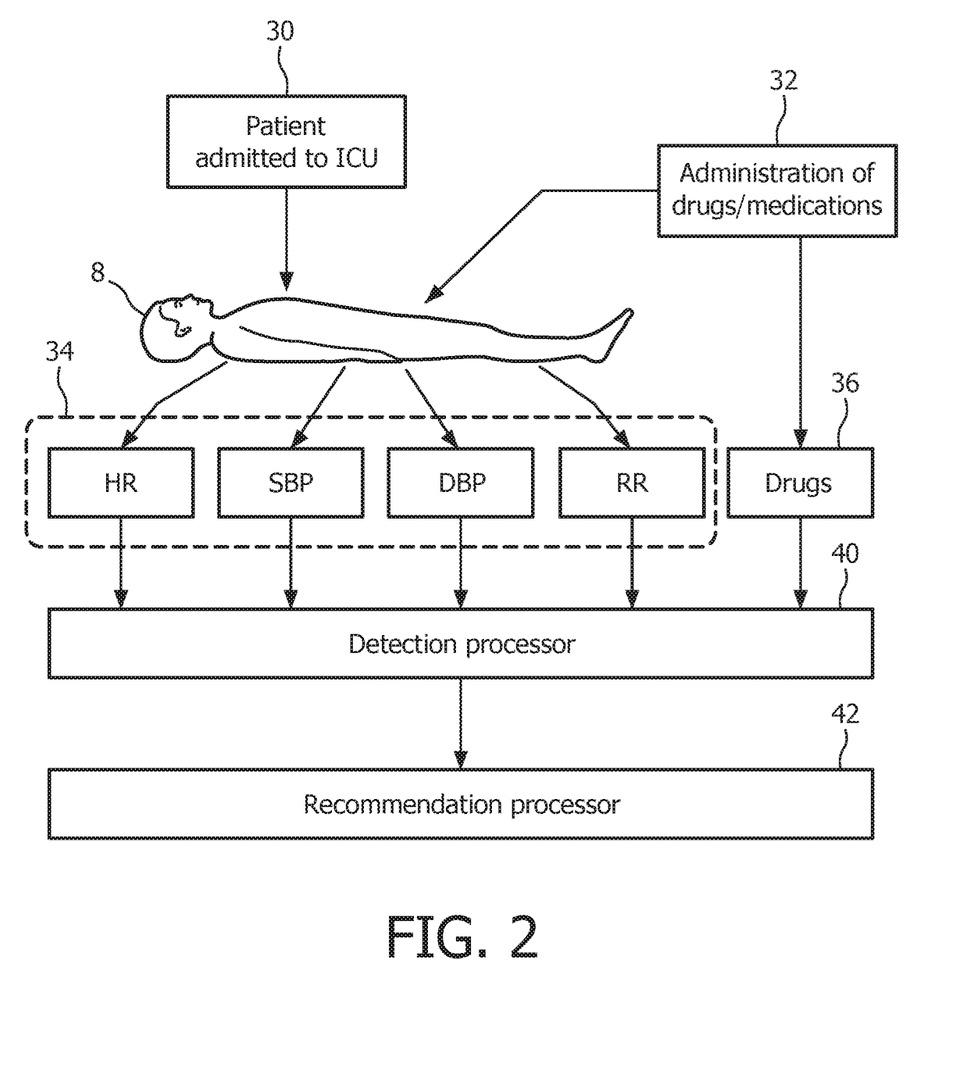
FIG. 2 illustrates an ARDS detection and ventilation recommendation approach.

Various embodiments of continuous ARDS detection are set forth in Vairavan et al., Int'l Appl. Pub. No. WO 2013/121374 A2 published Aug. 22, 2013 which is incorporated herein by reference in its entirety. For example, an embodiment employing Lempel-Ziv complexity-based detection of ARDS can be used. With reference to FIG. 2, the patient 8 is admitted to the ICU (indicated by block 30). There may be scenarios where different drugs/medications ("drugs" and "medications" are used interchangeably herein) may be administered to the patient 8 in order to stabilize the patient (indicated by block 32). Other therapies such as mechanical ventilation may also be administered. The illustrative ARDS detection approach of FIG. 2 utilizes illustrative vital signs data streams 34 including heart rate (HR), arterial systolic and diastolic blood pressure (SBP and DBP), and respiratory rate (RR), along with an additional patient data stream 36 comprising instances of the administration 32 of one or more different drugs to the patient 8. The drug administration data stream 36 can take various forms, such as a binary data stream (e.g. value "0" as a function of (optionally discretized) time except during a drug administration event which is indicated by a value "1". In the case of a drug administered over a time interval, e.g. an intravenous drip, the value may be "0" when no drip is being administered and "1" (or some other value) during the administration of the drip). Other value-time representations are also contemplated, e.g. a time-varying value modeling the expected dynamic drug concentration in the patient (or in an organ of interest) from initial administration until the drug is removed from the body by the kidneys or other mechanism.

From the data streams, a detection processor 40 continuously computes the ARDS score. The detection processor 40 can output the ARDS score over time in the form of a plot of the score over time. The detection processor 40 may, for example, employ an ARDS (or ALI) scoring algorithm such as one disclosed in WO 2013/121374 A2 published Aug. 22, 2013, for example in which linear discriminant analysis (LDA) or a voting system aggregates vital signs 34 and optionally other information (e.g. the illustrative drug administration information 36, laboratory results, ventilator settings, or so forth) to generate the ARDS score. The illustrative ARDS scores presented herein were generated using the detection processor 40 embodied as the LDA aggregation model of WO 2013/121374 A2 with data input including vital signs, laboratory test results, and ventilator settings, with output in the "probability-type" range [0, 1]. More generally, the detection processor 40 can use other ARDS scoring approaches that generate a score indicative of risk that the patient has, or is developing toward, Acute Respiratory Distress Syndrome. In some embodiments, the detection processor 40 may output in a range other than [0, 1], for example the output may be a "percentage-type" value in the range 0-100. A recommendation processor 42 monitors the ARDS score in view of a predetermined threshold and recommends interventional therapy, e.g. ventilation therapy/settings, for the patient based on the monitored score. When the recommendation processor 42 detects the patient 8 to be at high risk of ARDS, the recommendation processor 42 suggests possible therapy routes based on best clinical practice. The ventilation strategies are broadly classified as Traditional and Protective. The protective ventilation strategy has been shown in clinical studies to reduce mortality in ARDS patients. The ranges of values associated with the different ventilation strategy are given as:

| Mechanical Ventilation settings | Traditional | Protective |
| --- | --- | --- |
| Tidal Volume (VT) (ml/kg) | 10-15 | 4-8 |
| Positive End Expiratory Pressure (PEEP) (cm $H_2O$) | 5-12 | >12 |

Figure 3:
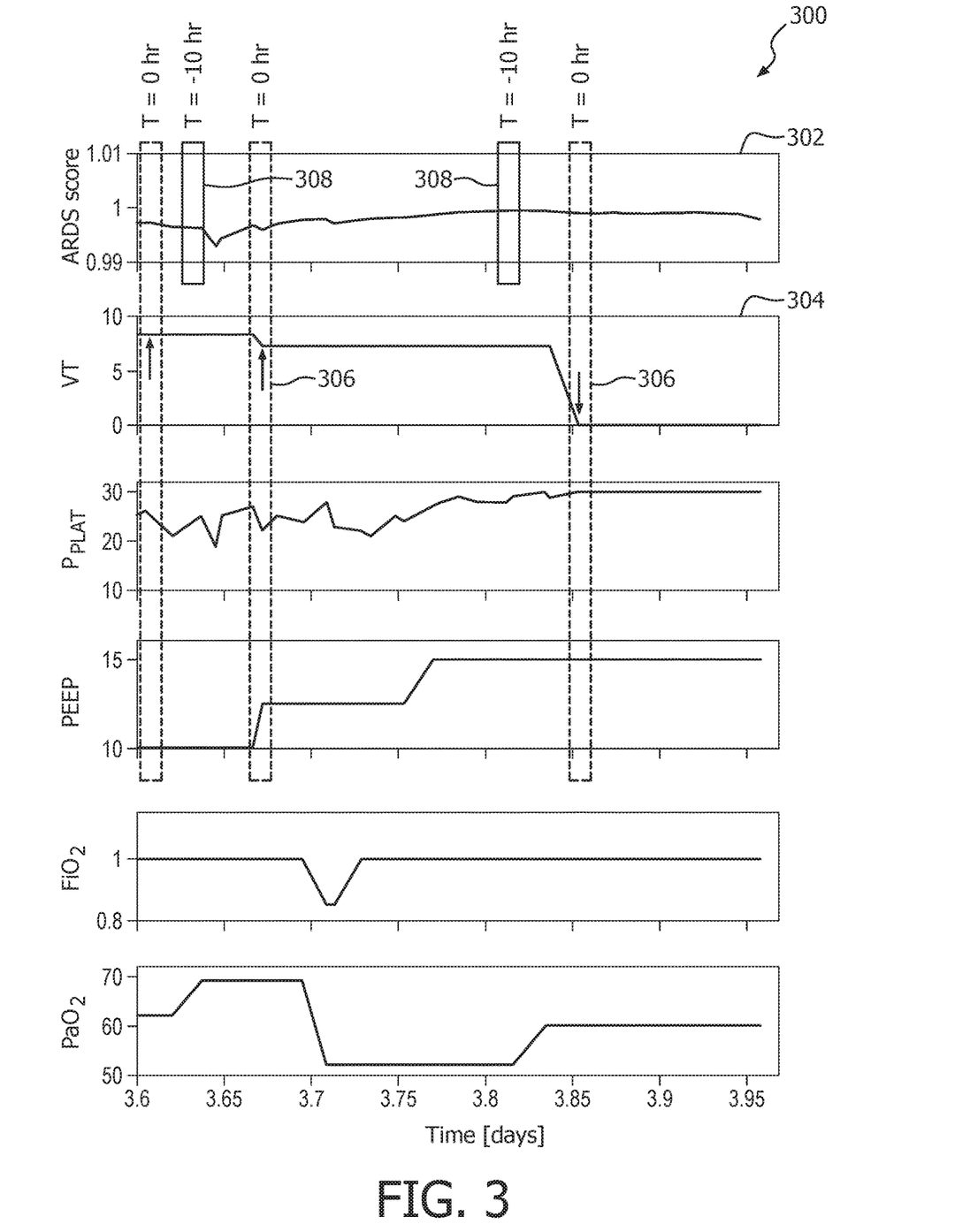
FIG. 3 illustrates a correlation of a monitored ARDS score and changes in ventilation strategy.
Figure 4:
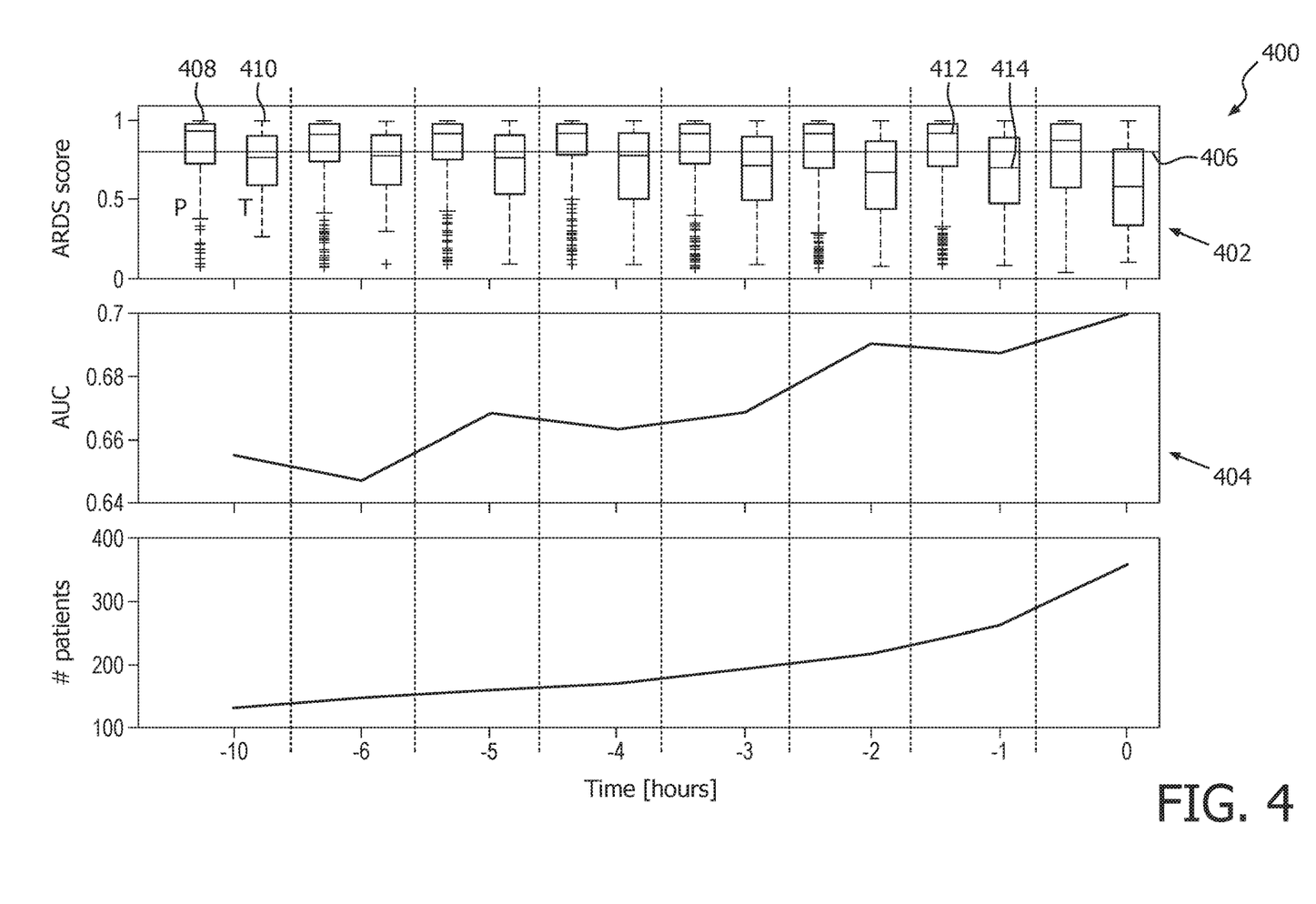
FIG. 4 illustrates comparison box plots of a traditional ventilation strategy and a protective ventilation strategy on an ARDS score in view of tidal volume settings.
Figure 5:
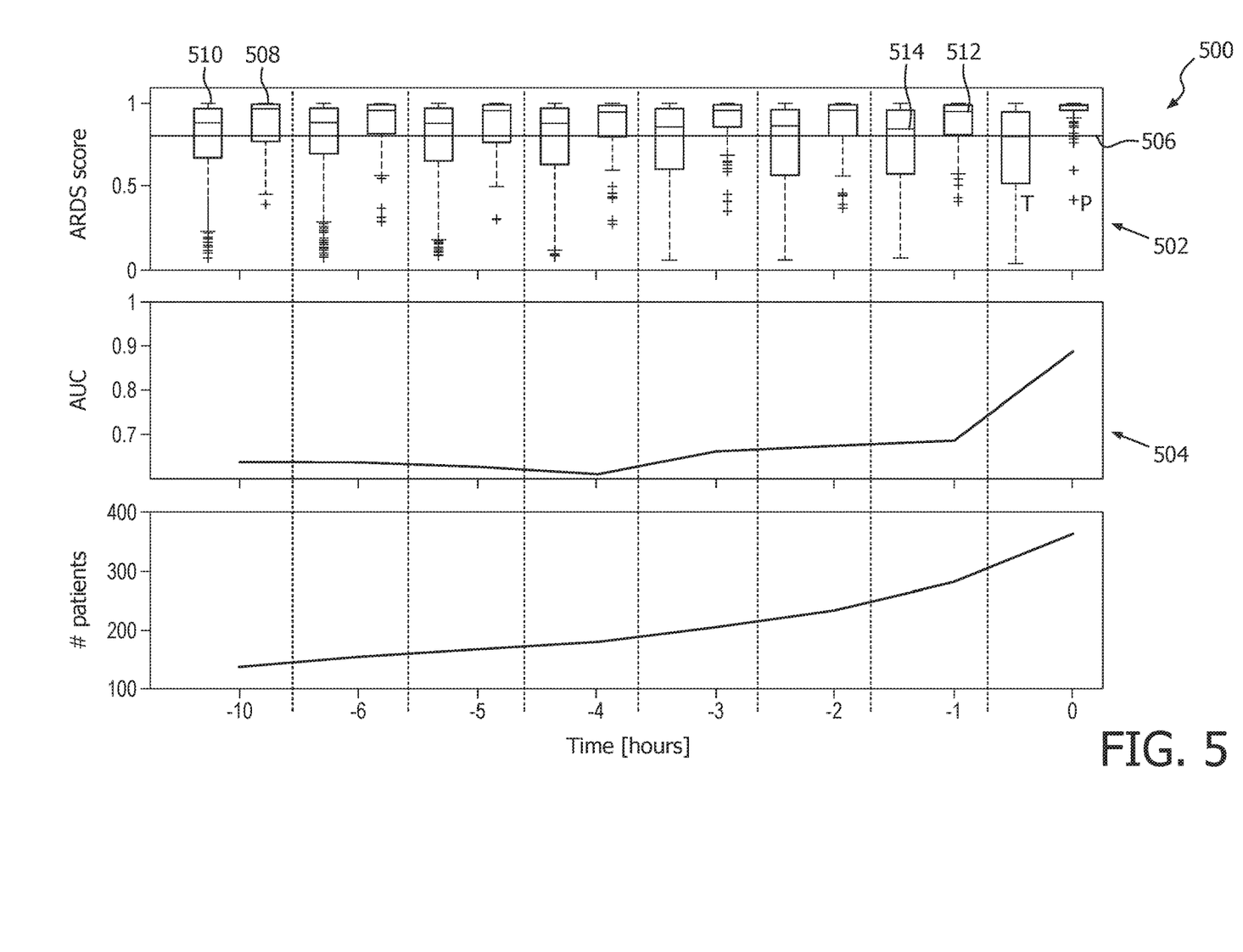
FIG. 5 illustrates comparison box plots of a traditional ventilation strategy and a protective ventilation strategy on an ARDS score in view of PEEP settings.

With reference to FIGS. 3-5, ARDS patient correlation results are shown demonstrating that the ARDS score is predictive of ventilator setting change instances. Correlation of ARDS score with ventilation strategy (Traditional or Protective via vent settings as shown in the above table) was assessed by taking values of both ARDS score and vent setting change instances (T=0 hr) across patient records. Correlation of vent strategy with ARDS score (several hours before a vent setting change) was assessed to determine the capability of ARDS score to predict a vent setting. The time periods of investigation were T=10, 6, 5, 4, 3, 2 and 1 hours prior to vent setting change. With reference to FIG. 3, ARDS score 302 is compared with ventilation strategy as represented by ventilator tidal volume (VT) 304. In FIG. 3, Ventilator Tidal Volume (VT) setting changes are marked with black arrows. The box 306 surrounding an arrow indicates the zone corresponding to T=0 hr (vent setting change). The box 308 represents ARDS score at T=-10 hr, or the zone corresponding to 10 hours prior to the VT settings change (at T=0 hr).

Based on these results, the recommendation processor 42 suitably derives predictive inferences by examining values of the ARDS score. The recommendation processor 42 evaluates the ARDS score and can thereby provide a recommended ventilator setting (or setting change, if the patient is already on mechanical ventilation) up to several hours before the physician would recommend the ventilation setting change in the absence of this analysis. The recommendation processor 42 monitors the current ARDS score of the patient and uses the predictive inferences to determine whether a change in the ventilation strategy should be recommended. FIG. 3 thus demonstrates that the ARDS score can be used as a biomarker for recommending ventilator settings for an ARDS patient. In FIG. 3, the following notation is used: VT: Tidal Volume; $P_{PLAT}$: Plateau pressure; PEEP: positive end expiratory pressure; FiO2: Fraction of inspired oxygen; PaO2: Partial pressure of oxygen in blood.

FIGS. 4 and 5 show box plots of ARDS scores obtained during different time zones 306, 308 and time zones between them, as depicted in FIG. 3. In FIGS. 4 and 5, box plots provide the $25^{th}$, $50^{th}$, $75^{th}$ percentile as well as outliers for the data.

With particular reference to FIG. 4, the correlation 400 of ARDS score 402 and tidal volume settings is depicted. The top plot 402 of FIG. 4 shows box plots of ARDS score corresponding to protective (P) and traditional (T) tidal volume settings at different times relative to the tidal volume setting changes at T=0 hr. The threshold 406 indicates the optimal threshold for ARDS detection as determined by Receiver Operating Characteristic curve (ROC) analysis. The middle plot 404 shows the Area under the curve (AUC) of the ROC for different prediction times. The bottom plot shows total number of patients at different time instants. In FIG. 4, Protective Ventilation Strategy (P) has tidal volume of 4-8 ml/kg, while the Traditional Ventilation Strategy (T) has tidal volume of 10-15 ml/kg.

As shown in FIG. 4, a statistical plot of the AUC 404 of the ROC depicts a quantification of separation between the two ventilation strategies. The time is depicted as T=0 at the right most edge and looking back to T=-10 hours on the left hand edge of the plots. The ARDS score 402 is plotted in relation to a predetermined ARDS threshold score 406. At T=0 the ARDS scores corresponding to Protective and Traditional tidal volume settings are separable with an AUC for the ROC of 0.70. The threshold 406 shown in FIG. 4 is the optimal threshold for ARDS detection based on the ROC analysis. The median values 412 in the Protective Strategy box plots are higher than this threshold 406. This indicates that higher ARDS score is correlated with Protective Tidal volume settings.

The median values 412 of the Protective strategy box plots are consistently higher than median values 414 of the Traditional strategy box plots. This relation is observed across all time zones (T=-10 . . . 0). The threshold 406 is chosen to optimally separate the median values 412 for the protective strategy box plots from the median values 414 for the Traditional strategy box plots. As further seen in FIG. 4, the AUC shows a good separation between the Protective and Traditional Tidal Volume Strategy across all time zones. These results indicate that the ARDS score could be used to recommend Protective tidal volume settings. Though the separation between the Protective and Traditional Tidal Volume Strategy tends to decrease for earlier time periods, the separation remains strong up until T=-2 hours (AUC=0.69). This suggests the ARDS score 402 has a predictive capacity up until 2 hours before the ventilation intervention at T=0 with the predictive power of the ARDS score decreasing for earlier periods of time.

Based on the results of FIG. 4, the threshold 406 of 0.81 is suitably applied by the recommendation processor 42 in order to determine whether to recommend a tidal volume of 4-8 ml/kg as per Protective therapy (appropriate if the ARDS score is above threshold 406). In some embodiments, in order to prevent alarm fatigue, ventilation therapy is recommended only when the ARDS score is high, in which case Protective ventilation therapy is recommended.

With reference to FIG. 5, the correlation 500 of ARDS score 502 and PEEP settings is depicted. The top plot 502 shows box plots of ARDS score corresponding to protective and traditional ventilation settings at different time relative to the tidal volume setting changes at T=0 hr. The threshold 506 indicates the optimal threshold for ARDS detection. The middle plot 504 shows the area under curve (AUC) 504 of the ROC curve for different prediction times. The bottom plot shows total number of patients at different time instants. In FIG. 5, P: Protective Ventilation Strategy (PEEP>12 cm $H_2O$), T: Traditional Ventilation Strategy (PEEP=5-12 cm $H_2O$).

It can be seen in FIG. 5 that a high ARDS score is correlative of Protective PEEP settings as opposed to Traditional PEEP settings. The median values 512 for the Protective therapy are higher than the median values 514 for the Traditional therapy. This trend is observable across different time periods starting from T=0 hr to T=-10 hr. However, the separation between the two groups (Protective and Traditional) tends to decrease as hours before the vent setting change increases. Thus the predictive nature of ARDS score on vent setting recommendations would also decrease.

In sum, as demonstrated in FIGS. 4 and 5, a high ARDS score correlates to low tidal volume settings and also correlates to high PEEP settings. These settings are the characteristic settings of lung protective ventilation. Thus, the results described with reference to FIGS. 3-5 demonstrate that ARDS score is suitable for providing a recommendation to ventilate using either the traditional or protective strategy, with this prediction being reliably made at least 2 hours in advance of when a physician would typically make such an adjustment.

Figure 6:
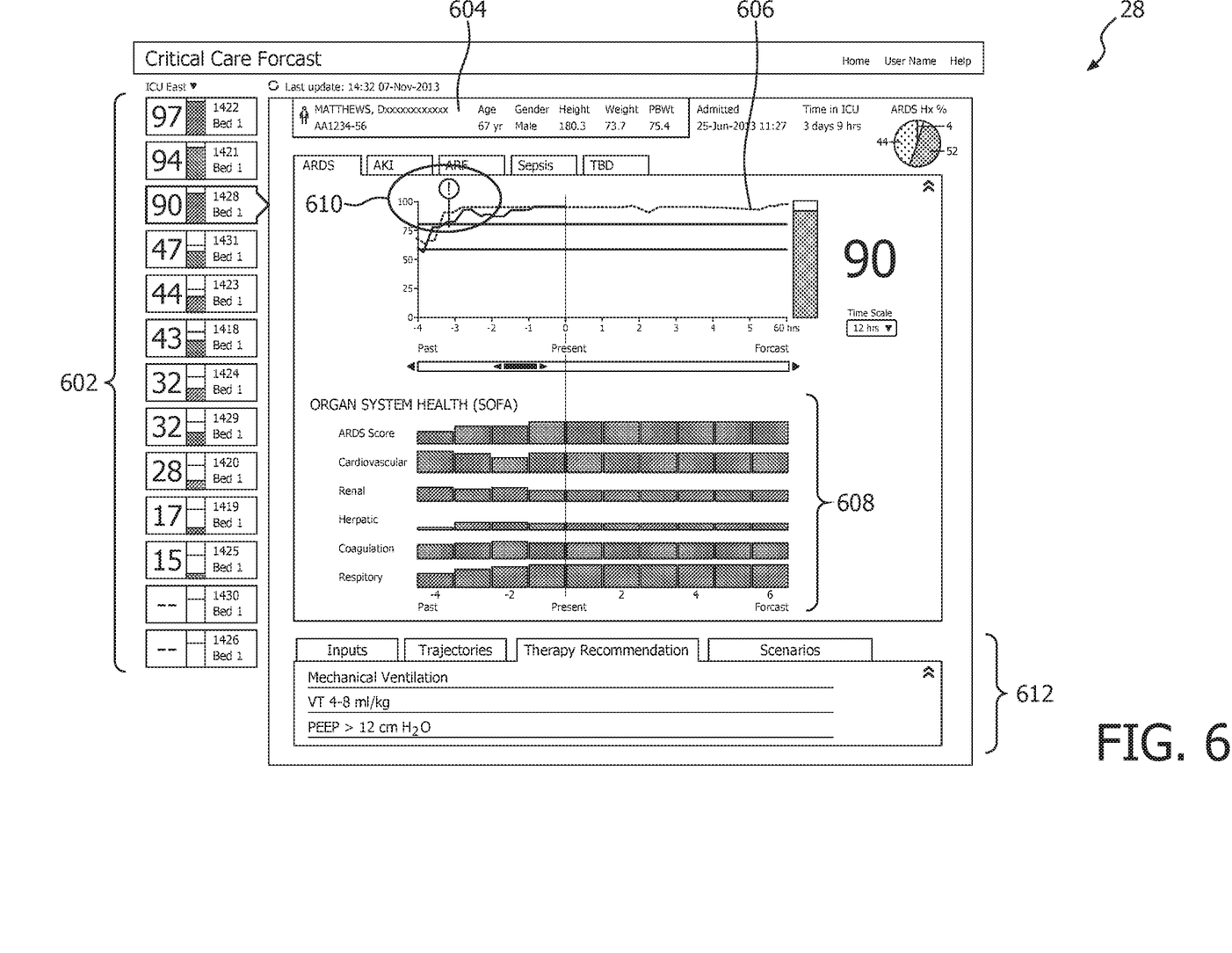
FIG. 6 illustrates an ARDS ventilation strategy tool.

With reference to FIG. 6, the recommendation processor 42 utilizes an ARDS ventilation recommendation tool 28 that provides a graphical user interface (GUI) for suggestions of lung protective ventilation as the ARDS risk increases above the decision threshold. The predictive nature of the ARDS score allows the ventilation recommendation tool 28 to advise users to apply low tidal volume settings and high PEEP settings up to 2-3 hours before healthcare providers would conventionally change the vent settings. It is contemplated that the above described analysis could be performed for other therapeutic interventions such as fluid administrations, and other mechanical ventilation settings such as Plateau Pressure, $FiO_2$, etc.

A panel, i.e. window, represents a selectable bed display 602 for each patient with current ARDS scores highlighted. Another panel represents the demographics 604 of the patient of a selected patient from the bed display 602. The ARDS score 606 (past, current and future trajectories) is displayed in parallel with the sequential organ failure assessment (SOFA) scores 608.

When the ARDS score 606 gets above a predetermined threshold, i.e. an optimal threshold based on retrospective analysis of the ARDS score history, an alert 610 is displayed in the screen. On clicking the alert 610, a therapy recommendation 612 is opened with detailed recommendations of lung protective ventilation settings to reduce the risk of ARDS. In one embodiment, the alert 610 is turned off when the healthcare providers view the therapy recommendation 612. Subsequent alerts will pop up each time the ARDS score 606 changes from a value below the threshold, e.g. 75 in this illustrative example, to a value greater than the threshold.

With returning reference to FIG. 1, the disclosed techniques for predicting ARDS or other conditions of concern for ICU patients are suitably implemented by the built-in computer, microprocessor, or so forth of the illustrative bedside monitor 10 and/or of the illustrative nurses' station electronic monitoring device 20. It will also be appreciated that the disclosed techniques can be embodied by a non-transitory storage medium storing instructions executable by such an electronic data processing device to perform the disclosed detection methods. The non-transitory storage medium may, for example, comprise a hard disk or other magnetic storage medium, random access memory (RAM), read-only memory (ROM), or another electronic storage medium, an optical disk or other optical storage medium, a combination of the foregoing, or so forth.

The disclosure has been set forth with reference to the preferred embodiments. Obviously, modifications and alterations will occur to others upon reading and understanding the preceding detailed description. It is intended that the present application be construed as including all such modifications and alterations insofar as they come within the scope of the appended claims or the equivalents thereof.

The invention claimed is:

1. A therapy guidance tool for acute respiratory distress syndrome intensive care settings comprising:
a display device; and
a processor configured to:
compute an Acute Respiratory Distress Syndrome (ARDS) score indicative of whether a patient has ARDS based on measured physiological variables of the patient;
generate a recommended ventilation strategy for the patient using a threshold based on ARDS score history, wherein the threshold is chosen to optimally separate median ARDS score values for protective strategy from median ARDS score values for traditional strategy and the recommended ventilation strategy is either a traditional ventilation strategy or a protective ventilation strategy; and
display a representation of the ventilation therapy recommendation on the display device.

2. The therapy guidance tool according to claim 1, wherein the ARDS score is computed by:
receiving values of a plurality of physiological variables for the patient;
computing the ARDS score based at least on the received values of the plurality of physiological variables for the patient; and
displaying a representation of the computed ARDS score on the display device.

3. The therapy guidance tool of claim 1, wherein the traditional ventilation strategy includes a recommended tidal volume of between 10 ml/kg and 15 ml/kg inclusive and the protective ventilation strategy includes a recommended tidal volume of between 4 ml/kg and 8 ml/kg inclusive.

4. The therapy guidance tool of claim 3, wherein the traditional ventilation strategy includes a recommended positive end-expiratory pressure (PEEP) of between 5 cm $H_2O$ and 12 cm $H_2O$ inclusive and the protective ventilation strategy includes a recommended PEEP of greater than 12 cm $H_2O$.

5. The therapy guidance tool of claim 4, wherein the processor is further configured to display the representation of the ventilation therapy recommendation on the display device with an indication of a time horizon for the ventilation therapy recommendation wherein the indicated time horizon is two hours or less.

6. The therapy guidance tool of claim 1, wherein the ARDS score is in a range [0,1] or a percentage in the range [0%, 100%] and the threshold is 0.8 or 80%.

7. The therapy guidance tool of claim 1, wherein the processor is further configured to compute the ARDS score continuously in real time.

8. The therapy guidance tool of claim 1, wherein the measured physiological variables of the patient include at least heart rate, respiration rate, and a blood pressure.

9. The therapy guidance tool of claim 1, wherein the processor is configured to display the representation of the recommendation of a ventilation strategy for the patient on the display device using a graphical user interface (GUI).

10. A method for treating a patient comprising:
monitoring physiological variables of the patient;
using a processor:
computing an Acute Respiratory Distress Syndrome (ARDS) score for the patient based on the monitored physiological variables, and
generating a mechanical ventilation recommendation for the patient using a threshold based on ARDS score history after the ARDS score is above the threshold, wherein the threshold is chosen to optimally separate median ARDS score values for protective strategy from median ARDS score values for traditional strategy; and displaying the mechanical ventilation recommendation for the patient on a display device.

11. The method of claim 10, wherein the monitored physiological variables include a heart rate, a respiration rate, and a blood pressure.

12. The method of claim 10, wherein the traditional ventilation settings include tidal volume between 10 ml/kg and 15 ml/kg inclusive and the protective ventilation settings include tidal volume between 4 ml/kg and 8 ml/kg inclusive.

13. The method of claim 10, wherein the protective ventilation settings include a Positive End-Expiratory Pressure (PEEP) of greater than 12 cm $H_2O$.

14. The method of claim 10, wherein the ARDS score is in a range [0,1] or a percentage in the range [0%, 100%] and the threshold is 0.8 or 80%.

15. The method of claim 10, further comprising:

displaying past, current, and future trajectories of the ARDS score.

* * * * *